United States Patent
Grammenos et al.

(10) Patent No.: US 6,696,607 B2
(45) Date of Patent: Feb. 24, 2004

(54) USE OF PHENETHYL ACRYLAMIDES, NOVEL PHENETHYL ACRYLAMIDES, METHOD FOR THE PRODUCTION THEREOF AND AGENTS CONTAINING THE SAME

(75) Inventors: Wassilios Grammenos, Ludwigshafen (DE); Hubert Sauter, Mannheim (DE); Oliver Cullmann, Heppenheim (DE); Markus Gewehr, Kastellaun (DE); Bernd Müller, Frankenthal (DE); Jordi Tormo i Blasco, Limburgerhof (DE); Norbert Götz, Worms (DE); Thorsten Volk, Mannheim (DE); Gisela Lorenz, Hambach (DE); Eberhard Ammermann, Heppenheim (DE); Reinhard Stierl, Mutterstadt (DE); Siegfried Strathmann, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/297,287

(22) PCT Filed: Jun. 13, 2001

(86) PCT No.: PCT/EP01/06686
§ 371 (c)(1),
(2), (4) Date: Dec. 4, 2002

(87) PCT Pub. No.: WO01/95721
PCT Pub. Date: Dec. 20, 2001

(65) Prior Publication Data
US 2003/0191190 A1 Oct. 9, 2003

(30) Foreign Application Priority Data
Jun. 14, 2000 (DE) .......................... 100 28 576

(51) Int. Cl.[7] ........................ C07C 233/09; A01N 37/18
(52) U.S. Cl. ........................ 564/182; 564/161; 514/617; 514/522; 558/414
(58) Field of Search ............................. 564/182; 514/617

(56) References Cited
U.S. PATENT DOCUMENTS 3,526,653 A 9/1970 Shen et al.
3,657,340 A 4/1972 Johnson et al.
6,130,251 A 10/2000 Seitz et al.

FOREIGN PATENT DOCUMENTS

| | | |
|---|---|---|
| EP | 407 217 | 1/1991 |
| EP | 529 736 | 3/1993 |
| WO | 93/01523 | 1/1993 |
| WO | 96/17825 | 6/1996 |
| WO | 96/23763 | 8/1996 |

OTHER PUBLICATIONS

Hererocycles,vol.25,1987,XP000566000, Hira et al.
JP2200–658, Abstract, 1990.
JP 3154–649, Abstract 1998.
JP 06080616, Abstract, 1994.

Primary Examiner—Shailendra Kumar
(74) Attorney, Agent, or Firm—Keil & Weinkauf

(57) ABSTRACT

Use of phenethylacrylamides of the formula I:

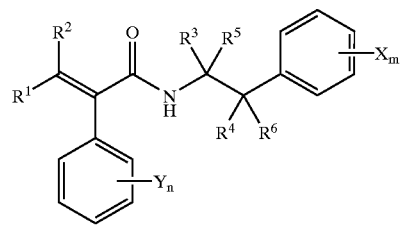

in which the substituents have the following meanings:
X is halogen, alkyl, haloalkyl, alkoxy, haloalkoxy and —O—C($R^a,R^b$)—C≡C—$R^c$;
$R^a,R^b$ and $R^c$ have the meanings given in the description;
m,n independently of one another are 1 to 4, it being possible for the radicals X or Y to be different if m or n is greater than 1;
Y is halogen, nitro, cyano, alkyl, $CF_3$, alkoxy and phenyl;
$R^1,R^2$ independently of one another are hydrogen, halogen, alkyl, alkoxy, haloalkoxy and $CF_3$;
$R^3,R^4,R^5,R^6$ independently of one another are hydrogen, halogen, alkyl, alkoxy, or
$R^3$ and $R^4$ together form a cyclopropyl ring, it being possible for the C—$R^5$— and C—$R^6$ bonds can be in the E- or Z-position relative to each other;
for controlling phytopathogenic fungal pests, novel phenethylacrylamides, their preparation, and compositions comprising them.

9 Claims, No Drawings

USE OF PHENETHYL ACRYLAMIDES, NOVEL PHENETHYL ACRYLAMIDES, METHOD FOR THE PRODUCTION THEREOF AND AGENTS CONTAINING THE SAME

This application is a 371 of PCT/EP01/06686, filed Jun. 13, 2001.

The present invention relates to the use of phenethylacrylamides of the formula I

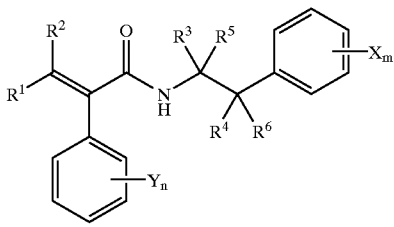

in which the substituents have the following meanings:

X is halogen, $C_1$–$C_4$-alkyl, $C_1$–$C_4$-haloalkyl, $C_1$–$C_8$-alkoxy, $C_1$–$C_4$-haloalkoxy and —O—C($R^a$,$R^b$)—C≡C—$R^c$;

$R^a$,$R^b$ independently of one another are hydrogen and $C_1$–$C_6$-alkyl;

$R^c$ is hydrogen, $C_1$–$C_8$-alkyl, $C_3$–$C_8$-cycloalkyl and phenyl which can be substituted by halogen, cyano, nitro, $CF_3$, $C_1$–$C_4$-alkyl and/or $C_1$–$C_4$-alkoxy;

m,n independently of one another are 1 to 4, it being possible for the radicals X and Y to be different if m or n is greater than 1;

Y is halogen, nitro, cyano, $C_1$–$C_4$-alkyl, $CF_3$, $C_1$–$C_4$-alkoxy and phenyl;

$R^1$, $R^2$ independently of one another are hydrogen, halogen, $C_1$–$C_4$-alkyl, $C_1$–$C_4$-alkoxy, $C_1$–$C_4$-haloalkoxy and $CF_3$;

$R^3$,$R^4$,$R^5$,$R^6$ independently of one another are hydrogen, $C_1$–$C_4$-alkyl and $C_1$–$C_4$-alkoxy or $R^3$ and $R^4$ together form a cyclopropyl ring, it being possible for the C—$R^5$— and C—$R^6$-bonds to be in the E- or Z-position relative to each other;

for controlling phytopathogenic fungal pests.

The invention furthermore relates to novel phenethylacrylamides, to processes for their preparation, and to compositions comprising them.

Various arylacrylamides are disclosed in EP-A 407 217, EP-A 529 736, WO-A 93/01523, JP-A 06/080 616, U.S. Pat. No. 3,657,340, U.S. Pat. No. 3,526,653 and JP-A 63/154 649. Some of them are described as herbicides. However, their fungicidal action is unknown in the prior art.

α-Oximinophenylacetic acid arylamides are described in WO-A 96/17825 and WO-A 96/23763 as fungicides and in JP 02/200 658 as herbicides. In WO-A 96/17825, arylacrylamides are only covered by the general disclosure.

However, the fungicidal action of the [lacuna] described in the abovementioned documents is not satisfactory in many cases. It is therefore an object of the invention to find compounds with an improved action.

It has been found that this object is achieved by the use of the phenylethylacrylamides of the Formula I as fungicides and the novel phenethylacrylamides, and compositions comprising them.

The phenethylacrylamides of the formula I can be prepared by the synthetic routes described in EP-A 407 217, EP-A 529 736, WO-A 93/01523, JP-A 06/080 616, U.S. Pat. No. 3,657,340, U.S. Pat. No. 3,526,653 and JP-A 63/154 649 whose disclosure is herewith incorporated.

The novel phenethylacrylamides in which $R^1$ and $R^2$ are identical and are Cl, F and $CH_3$ can be obtained, for example, starting from α-keto esters of the formula II where R is $C_1$–$C_4$-alkyl by the routes described hereinbelow:

Compounds in which $R^1$ and $R^2$ are chlorine are obtained by reacting α-keto esters of the formula II with triphenylphosphine ($PPh_3$) and $CCl_4$ to give acrylic esters of the formula IIIa. This reaction is usually carried out at temperatures from 10° C. to 120° C., preferably 20° C. to 80° C., in an inert organic solvent [cf. tetrahedron Lett., p. 3003 et seq., 1988].

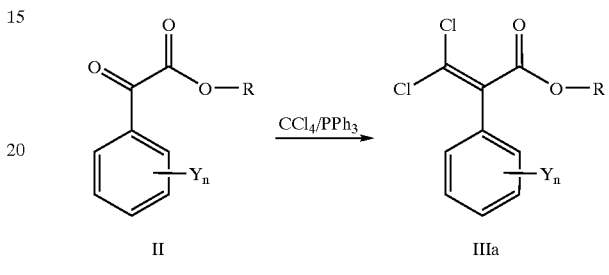

Suitable solvents are aromatic hydrocarbons such as toluene, o-, m- and p-xylene, halogenated hydrocarbons such as methylene chloride, chloroform, and chlorobenzene, nitriles such as acetonitrile and propionitrile, and dimethyl sulfoxide, dimethyl formamide and dimethyl acetamide, especially preferably acetonitrile and propionitrile. Mixtures of these may also be used.

In general, the starting materials are reacted with each other in equimolar amounts. It may be advantageous for the yield to employ $CCl_4$ and $PPh_3$ in excess based on II.

Compounds in which $R^1$ and $R^2$ are fluorine are obtained by reacting α-keto esters of the formula II with diphenyl-1,1-difluoromethylphosphine of the formula VI where Ph is phenyl, to give acrylic esters of the formula IIIb. This reaction is usually carried out at temperatures from −70° C. to +80° C., preferably 0° C. to 20° C., in an inert organic solvent in the presence of a base [cf. tetrahedron Lett., p. 5571 et seq., 1990].

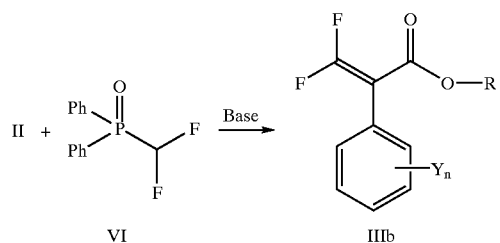

Suitable solvents are ethers such as diethyl ether, diisopropyl ether, tert-butylmethyl ether, dioxane, anisole and tetrahydrofuran, especially preferably diethyl ether and tetrahydrofuran. Mixtures of these may also be used.

Suitable bases are, generally, inorganic compounds such as alkali metal hydrides and alkaline earth metal hydrides such as lithium hydride, sodium hydride, potassium hydride and calcium hydride, alkali metal amides such as lithium amide, sodium amide and potassium amide, organo metal compounds, in particular alkali metal alkyls such as methyllithium, butyllithium, lithiumdiisopropylamine (LDA) and phenyllithium. Butyllithium and LDA are especially preferred.

In general, the bases are employed in catalytic amounts, and they may also be used in equimolar amounts, in excess or, if appropriate, as solvents.

In general, the starting materials are reacted with each other in equimolar amounts. It may be advantageous for the yield to employ VI in an excess based on II.

Alternatively, compounds in which $R^1$ and $R^2$ are fluorine, may also be obtained by reacting α-keto esters of the formula II with sodium 2-chloro-2,2-difluoroacetate, of the formula VII, and triphenylphosphine ($PPh_3$) to give acrylic esters of the formula IIIb. This reaction is usually carried out at temperatures from 20° C. to 180° C., preferably 60° C. to 180° C., in an inert organic solvent [cf. Org. Synth. Vol. V, p. 949 et seq. (1973)].

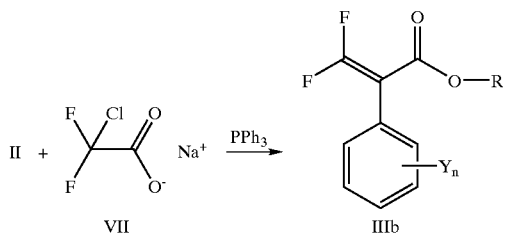

Suitable solvents are aromatic hydrocarbons such as toluene, o-, m- and p-xylene, ethers such as diethyl ether, diisopropyl ether, tert-butyl methyl ether, dioxane, anisole, tetrahydrofuran (THF), ethylene glycol dimethyl ether, diethylene glycol dimethyl ether and 1,2-diethoxyethane, nitrites such as acetonitrile and propionitrile, and also dimethyl sulfoxide, dimethylformamide and dimethylacetamide, especially preferably THF and diethylene glycol dimethyl ether. Mixtures of these may also be used.

In general, the starting materials are reacted with each other in equimolar amounts. It may be advantageous for the yield to employ VII in an excess based on II.

Compounds in which $R^1$ and $R^2$ are methyl are obtained by reacting α-keto esters of the formula II with isopropylphosphonium halide of the formula VIII in the sense of a Wittig reaction. Preferred as halides of the formula VIII are iodides and bromides.

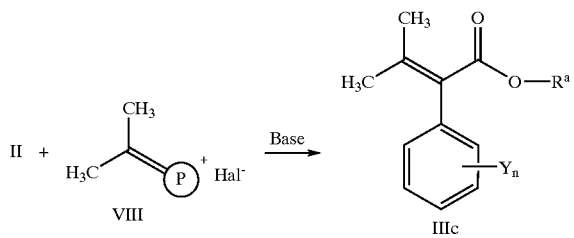

In the above reaction scheme, Ⓟ in the formula VIII is a phosphoranyl radical, such as, for example, triphenylphosphoranyl.

The Wittig reaction is usually carried out at temperatures from −78° C. to +85° C., preferably −10° C. to +65° C., in an inert organic solvent in the presence of a base [cf. Can. J. Chem. 1971, p. 2143 et seq.].

Suitable solvents are aromatic hydrocarbons such as toluene, o-, m- and p-xylene, ethers such as diethyl ether, diisopropyl ether, tert-butyl methyl ether, dioxane, anisole and tetrahydrofuran (THF), nitrites such as acetonitrile and propionitrile, and also dimethyl sulfoxide, dimethylformamide and dimethylacetamide, especially preferably diethyl ether and THF. Mixtures of these may also be used.

Suitable bases are, generally, inorganic compounds such as alkali metal hydrides and alkaline earth metal hydrides such as lithium hydride, sodium hydride, potassium hydride and calcium hydride, alkali metal amides such as lithium amide, sodium amide and potassium amide, organometal compounds, in particular alkali metal alkyls such as methyllithium, butyllithium, and phenyllithium, alkali metal alkoxides and alkaline earth metal alkoxides such as sodium methoxide, sodium ethoxide, potassium ethoxide, potassium tert-butoxide and dimethoxymagnesium. Sodium hydride and sodium methoxide are especially preferred.

In general, the bases are employed in catalytic amounts, but they may also be used in equimolar amounts, in excess or, if appropriate, as solvent.

In general, the starting materials are reacted with each other in equimolar amounts. It may be advantageous for the yield to employ VIII in an excess based on II.

Carboxylic esters of the formula III in which $R^1$ and $R^2$ are identical and are Cl, F and $CH_3$ are hydrolyzed by customary methods to give the carboxylic acids of the formula IV [cf. Organikum [Organic Chemistry], 16th Edition, p. 415 and 622, VEB Deutscher Verlag der Wissenschaften, Berlin 1985]. This reaction is usually carried out at temperatures from 10° C. to 80° C., preferably 20° C. to 60° C., in an inert organic solvent in the presence of a base such as alkali metal hydroxides or alkaline earth metal hydroxides, in particular sodium hydroxide or potassium hydroxide.

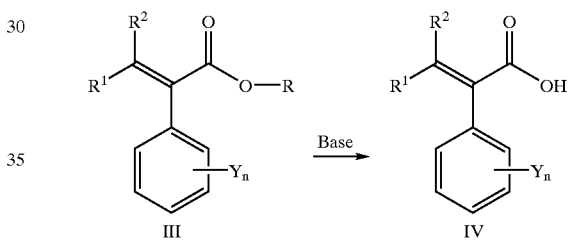

Carboxylic acids of the formula IV can be amidated in the known manner directly with phenethylamines of the formula V to give the compounds of the formula I [cf. Houben-Weyl, Methoden der Organischen Chemie, [Methods in Organic Chemistry], Vol. E5, pp. 941–972, Georg Thieme Verlag Stuttgart and New York 1985].

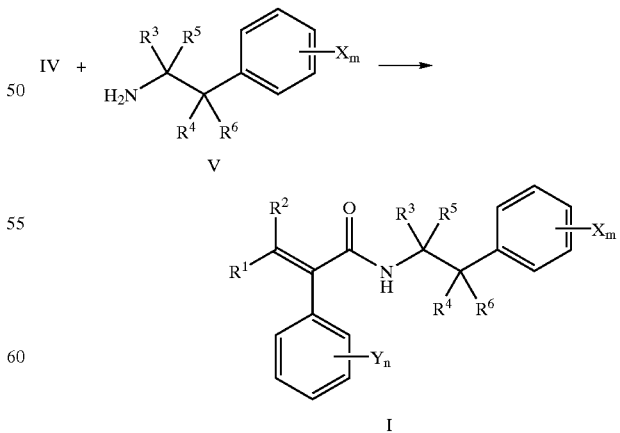

In general, the starting materials are reacted with each other in equimolar amounts. It may be advantageous for the yield to employ V in an excess based on IV.

Alternatively, carboxylic acids of the formula IV may first be activated prior to amidation with V, for example by converting them into acyl halides, in particular acyl chlorides of the formula IVa.

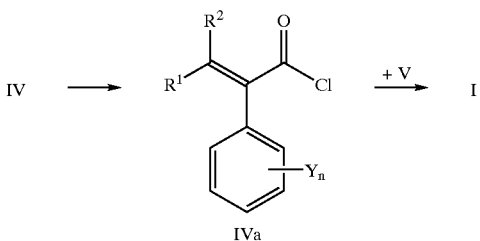

The chlorination of carboxylic acids IV is usually carried out at temperatures from −20° C. to 100° C., preferably −10° C. to 80° C., in an inert organic solvent [cf. Organikum, 16th Edition, p. 423 et seq., VEB Deutscher Verlag der Wissenschaften, Berlin 1985].

Chlorinating agents which are suitable for this reaction are the customary inorganic or organic chlorinating agents, for example thionyl chloride, oxalyl chloride, phosphorus trichloride, phosphorus pentachloride, phosphorus oxychloride, triphenylphosphine/$CCl_4$, preferably thionyl chloride.

Solvents which are suitable are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide, dimethylformamide and dimethylacetamide, especially preferably acetonitrile, toluene and tetrahydrofuran. Mixtures of these may also be used.

In general, the chlorinating agents are employed in at least equimolar amounts. It may be advantageous for the yield to employ them in an excess of up to 10 mol per mol of IV, preferably up to 5 mol, in particular up to 3 mol.

The amidation of the acyl halides with the phenethylamine of the formula V is carried out as illustrated, for example, for the compound IVa:

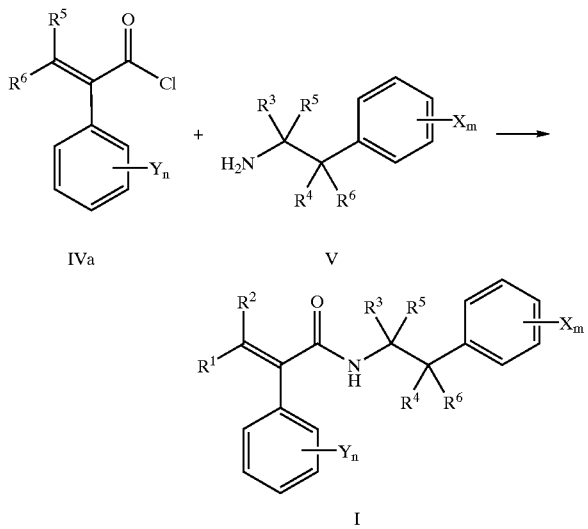

This reaction is usually carried out at temperatures of 0° C. to 80° C., preferably 20° C. to 40° C., in an inert organic solvent in the presence of a base [cf. Organikum, 16th Edition, p. 412 et seq., VEB Deutscher Verlag der Wissenschaften, Berlin 1985].

Suitable solvents are ethers such as diethyl ether, diisopropyl ether, tert-butyl methyl ether, dioxane, anisole and THF, nitrites such as acetonitrile and propionitrile, and also dimethyl sulfoxide, dimethylformamide and dimethylacetamide, especially preferably diethyl ether and THF. Mixtures of these may also be used.

Bases which can be used are, generally, inorganic compounds such as alkali metal carbonates and alkaline earth metal carbonates such as lithium carbonate, potassium carbonate and calcium carbonate, and also alkali metal hydrogen carbonates such as sodium hydrogen carbonate, furthermore organic bases, for example tertiary amines such as trimethylamine, triethylamine, tri-isopropylethylamine and N-methylpiperidine, pyridine, substituted pyridines such as collidine, lutidine and 4-dimethylaminopyridine, and bicyclic amines. Triethylamine and pyridine are especially preferred.

In general, the bases are employed in catalytic amounts, but they may also be used in equimolar amounts, in excess or, if appropriate, as solvent.

In general, the starting materials are reacted with each other in equimolar amounts. It may be advantageous for the yield to employ V in an excess based on IVa.

The starting materials of the formula II which are required for the preparation of the compounds I are known from the literature, for example commercially available, or can be prepared via the following routes:

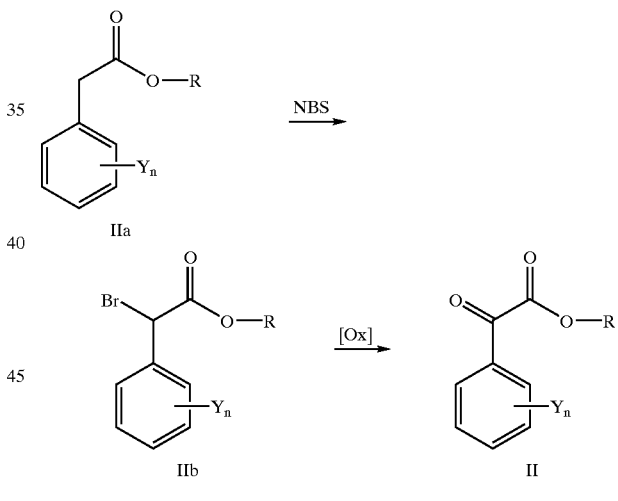

The bromination with N-bromosuccinimide (NBS) or 1,3-dibromo-5,5-dimethylhydrantoin is usually carried out at temperatures of 0° C. to 200° C., preferably 20° C. to 110° C., in an inert organic solvent in the presence of a free-radical initiator [cf. Synthetic Reagents, Vol. 2, pp. 1–63, Wiley, New York (1974); J. Heterocyclic Chem. pp. 1431–1436 (1993); Synth. Commun. p. 2803 et seq. (1996); J. Med. Chem. p. 481 et seq. (1981)].

The bromine compounds IIb are oxidized directly to give α-keto esters II. The oxidation with N-methylmorpholine oxide or p-dimethylaminopyridine oxide is usually carried out at temperatures of 0° C. to 100° C., preferably 20° C. to 60° C., in dimethylsulfoxide [cf. Bull. Chem. Soc. Jpn., p. 2221 (1981)].

As an alternative, phenyl acetic esters IIa can also be oxidized directly to give α-keto esters II. The oxidation can be carried out, for example, with $SeO_2$ or $KMnO_4$; it is usually carried out at temperatures of 20° C. to 180° C., preferably 20° C. to 120° C., in an inert organic solvent [cf. Synthesis, p. 915 (1994); Synth Commun., p. 1253 (1988); J. Gen. Chem. USSR, Vol. 21, p. 694 et seq. (1951)].

The phenyl acetic esters Ia which are required for the preparation of the compounds II are known from the literature or commercially available.

Those specific compounds I which are not accessible by the above-described routes can be prepared by derivatization of other compounds I.

If the synthesis yields isomer mixtures, their separation is, however, generally not absolutely necessary since some of the individual isomers can be converted into each other during processing for use or upon use (for example when exposed to light, acids or bases). Corresponding conversions may also take place after application, for example in the case of plant treatment in the treated plants or in the fungal or animal pests to be controlled.

The reaction mixtures are processed in the customary manner, for example by mixing with water, phase separation and, if appropriate, chromatographic purification of the crude products. In some cases, the intermediate and end products are obtained in the form of colorless or pale brown, viscous oils which are freed or purified of volatile components under reduced pressure and at moderately elevated temperature. If the intermediates and end products are obtained as solids, they can also be purified by recrystallization or digestion.

Collective terms which generally represent the following substituents were used in the definitions of the symbols stated for the above formulae:

halogen: fluorine, chlorine, bromine and iodine;

alkyl: saturated, straight-chain or branched hydrocarbon radicals having 1 to 4 carbon atoms, for example methyl, ethyl, propyl, 1-methylethyl, butyl, 1-methylpropyl, 2-methylpropyl, 1,1-dimethylethyl;

haloalkyl: straight-chain or branched alkyl groups having 1 to 4 carbon atoms (as mentioned above), it being possible for some or all of the hydrogen atoms in these groups to be replaced by halogen atoms as mentioned above, for example $C_1-C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 8 carbon atoms (as mentioned above) which are bound to the skeleton via an oxygen atom (—O—);

haloalkoxy: straight-chain or branched haloalkyl groups having 1 to 4 carbon atoms (as mentioned above) which are bound to the skeleton via an oxygen atom (—O—);

Taking into consideration the intended use of the phenethylacrylamides of the formula I, the following meanings of the substituents, in each case alone or in combination, are especially preferred:

Those embodiments of the intermediates which are especially preferred with regard to the variables correspond to those of the radicals $X_m$, $Y_n$, $R^1$, $R^2$, $R^3$, $R^4$, $R^5$ and $R^6$ of the formula I.

Especially preferred compounds I are those in which $R^1$ and $R^2$ are identical and are chlorine, fluorine or methyl.

Other compounds I which are especially preferred are those in which $R^1$ and $R^2$ are chlorine.

Likewise especially preferred compounds I are those in which $R^1$ and $R^2$ are fluorine.

Especially preferred compounds I are furthermore those in which $R^1$ and $R^2$ are methyl.

Other especially preferred compounds of the formula I are those in which $R^1$ and $R^2$ are different, in particular those in which $R^1$ is a bulkier radical than $R^2$.

Likewise especially preferred are compounds of the formula I in which $R^2$ is hydrogen.

Moreover, especially preferred compounds I are those in which m is 1 or 2 and X is in 3-, 4- or 3,4-position.

Other especially preferred compounds of the formula I are those in which $X_m$ is 3–$C_1$–$C_4$-alkoxy, 4-O—C($R^a$,$R^b$)—C≡C—$R^c$. These compounds have the formula I'; in this formula, X' is $C_1$–$C_4$-alkoxy.

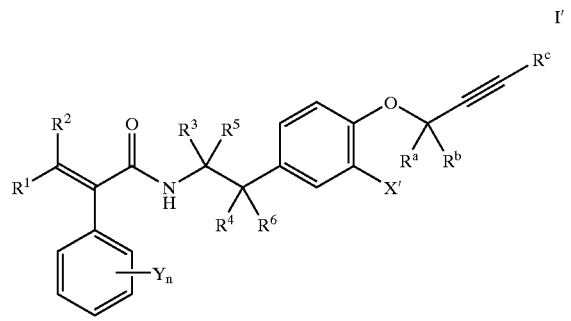

I'

Likewise especially preferred compounds I are those in which n is 1 or 2 and Y is in the 3-, 4- or 3,4-position.

In addition, especially preferred compounds I are those in which X is $C_1$–$C_8$-alkoxy and Y is halogen.

Moreover, compounds of the formula I which are especially preferred are those in which X is 3-methoxy.

Especially preferred compounds I are those in which $R^3$ to $R^6$ are hydrogen; these compounds correspond to the formula I.1:

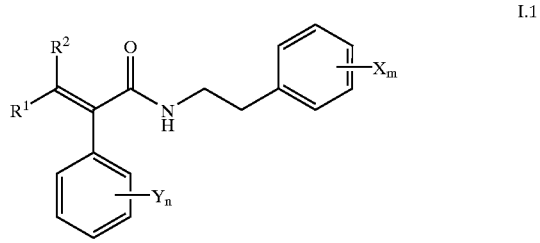

I.1

Moreover, especially preferred compounds I are those in which $R^5$ and $R^6$ are hydrogen; these compounds correspond to the formula I.2:

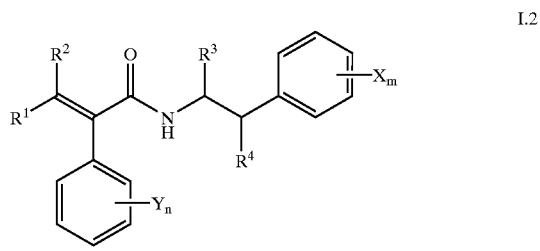

I.2

Likewise especially preferred compounds of the formula I.2 are those in which $R^1$ and $R^2$ are in each case identical and are chlorine, fluorine or methyl, $R^3$ and $R^4$ are hydrogen or together form a cyclopropyl ring, $Y_n$ is in the 4-, 3,4- or 2,4-position and is chlorine, fluorine, methyl or ethyl, X is chlorine, fluorine, $C_1$–$C_3$-alkyl, $C_1$–$C_3$-alkoxy, benzyloxy, allyloxy, propargyloxy, trifluoromethoxy or difluoromethoxy and m is 1 or 2, wherein, if m is 2, X is in the 3,4-position.

Particularly preferred with regard to their use are the compounds I which are compiled in the tables which follow. In addition, the groups mentioned in the tables for a substituent are per se, independently of the combination in which they are mentioned, an especially preferred embodiment of the substituent in question.

TABLE 1
Compounds of the formula I.1 in which $R^1$ and $R^2$ are chlorine and $Y_n$ is 4-chloro and the radical $X_m$ corresponds to one line of Table A for each compound.

TABLE 2
Compounds of the formula I.1 in which $R^1$ and $R^2$ are chlorine and $Y_n$ is 3,4-dichloro and the radical $X_m$ corresponds to one line of Table A for each compound.

TABLE 3
Compounds of the formula I.1 in which $R^1$ and $R^2$ are chlorine and $Y_n$ is 2,4-dichloro and the radical $X_m$ corresponds to one line of Table A for each compound.

TABLE 4
Compounds of the formula I.1 in which $R^1$ and $R^2$ are chlorine and $Y_n$ is 4-fluoro and the radical $X_m$ corresponds to one line of Table A for each compound.

TABLE 5
Compounds of the formula I.1 in which $R^1$ and $R^2$ are chlorine and $Y_n$ is 3,4-difluoro and the radical $X_m$ corresponds to one line of Table A for each compound.

TABLE 6
Compounds of the formula I.1 in which $R^1$ and $R^2$ are chlorine and $Y_n$ is 2,4-difluoro and the radical $X_m$ corresponds to one line of Table A for each compound.

TABLE 7
Compounds of the formula I.1 in which $R^1$ and $R^2$ are chlorine and $Y_n$ is 4-$CH_3$ and the radical $X_m$ corresponds to one line of Table A for each compound.

TABLE 8
Compounds of the formula I.1 in which $R^1$ and $R^2$ are chlorine and $Y_n$ is 3,4-$(CH_3)_2$ and the radical $X_m$ corresponds to one line of Table A for each compound.

TABLE 9
Compounds of the formula I.1 in which $R^1$ and $R^2$ are chlorine and $Y_n$ is 2,4-$(CH_3)_2$ and the radical $X_m$ corresponds to one line of Table A for each compound.

TABLE 10
Compounds of the formula I.1 in which $R^1$ and $R^2$ are chlorine and $Y_n$ is 4-$CH_2CH_3$ and the radical $X_m$ corresponds to one line of Table A for each compound.

TABLE 11
Compounds of the formula I.1 in which $R^1$ and $R^2$ are chlorine and $Y_n$ is 3,4-$(CH_2CH_3)_2$ and the radical $X_m$ corresponds to one line of Table A for each compound.

TABLE 12
Compounds of the formula I.1 in which $R^1$ and $R^2$ are chlorine and $Y_n$ is 2,4-$(CH_2CH_3)_2$ and the radical $X_m$ corresponds to one line of Table A for each compound.

TABLE 13
Compounds of the formula I.1 in which $R^1$ and $R^2$ are chlorine and $Y_n$ is 4-$CH(CH_3)_2$ and the radical $X_m$ corresponds to one line of Table A for each compound.

TABLE 14
Compounds of the formula I.1 in which $R^1$ and $R^2$ are chlorine and $Y_n$ is 4-$C(CH_3)_3$ and the radical $X_m$ corresponds to one line of Table A for each compound.

TABLE 15
Compounds of the formula I.1 in which $R^1$ and $R^2$ are chlorine and $Y_n$ is 4-$CF_3$ and the radical $X_m$ corresponds to one line of Table A for each compound.

TABLE 16
Compounds of the formula I.1 in which $R^1$ and $R^2$ are chlorine and $Y_n$ is 3,4-$(CH_3)_2$ and the radical $X_m$ corresponds to one line of Table A for each compound.

TABLE 17
Compounds of the formula I.1 in which $R^1$ and $R^2$ are chlorine and $Y_n$ is 2,4-$(CF_3)_2$ and the radical $X_m$ corresponds to one line of Table A for each compound.

TABLE 18
Compounds of the formula I.1 in which $R^1$ and $R^2$ are chlorine and $Y_n$ is 4-$OCH_3$ and the radical $X_m$ corresponds to one line of Table A for each compound.

TABLE 19

Compounds of the formula I.1 in which $R^1$ and $R^2$ are chlorine and $Y_n$ is 3,4-$(OCH_3)_2$ and the radical $X_m$ corresponds to one line of Table A for each compound.

TABLE 20

Compounds of the formula I.1 in which $R^1$ and $R^2$ are chlorine and $Y_n$ is 2,4-$(OCH_3)_2$ and the radical $X_m$ corresponds to one line of Table A for each compound.

TABLE 21

Compounds of the formula I.1 in which $R^1$ and $R^2$ are chlorine and $Y_n$ is 4-$OCF_3$ and the radical $X_m$ corresponds to one line of Table A for each compound.

TABLE 22

Compounds of the formula I.1 in which $R^1$ and $R^2$ are chlorine and $Y_n$ is 4-$OCHF_2$ and the radical $X_m$ corresponds to one line of Table A for each compound.

TABLE 23

Compounds of the formula I.1 in which $R^1$ and $R^2$ are chlorine and $Y_n$ is 4-phenyl and the radical $X_m$ corresponds to one line of Table A for each compound.

TABLE 24

Compounds of the formula I.1 in which $R^1$ and $R^2$ are fluorine and $Y_n$ is 4-chloro and the radical $X_m$ corresponds to one line of Table A for each compound.

TABLE 25

Compounds of the formula I.1 in which $R^1$ and $R^2$ are fluorine and $Y_n$ is 3,4-dichloro and the radical $X_m$ corresponds to one line of Table A for each compound.

TABLE 26

Compounds of the formula I.1 in which $R^1$ and $R^2$ are fluorine and $Y_n$ is 2,4-dichloro and the radical $X_m$ corresponds to one line of Table A for each compound.

TABLE 27

Compounds of the formula I.1 in which $R^1$ and $R^2$ are fluorine and $Y_n$ is 4-fluoro and the radical $X_m$ corresponds to one line of Table A for each compound.

TABLE 28

Compounds of the formula I.1 in which $R^1$ and $R^2$ are fluorine and $Y_n$ is 3,4-difluoro and the radical $X_m$ corresponds to one line of Table A for each compound.

TABLE 29

Compounds of the formula I.1 in which $R^1$ and $R^2$ are fluorine and $Y_n$ is 2,4-difluoro and the radical $X_m$ corresponds to one line of Table A for each compound.

TABLE 30

Compounds of the formula I.1 in which $R^1$ and $R^2$ are fluorine and $Y_n$ is 4-$CH_3$ and the radical $X_m$ corresponds to one line of Table A for each compound.

TABLE 31

Compounds of the formula I.1 in which $R^1$ and $R^2$ are fluorine and $Y_n$ is 3,4-$(CH_3)_2$ and the radical $X_m$ corresponds to one line of Table A for each compound.

TABLE 32

Compounds of the formula I.1 in which $R^1$ and $R^2$ are fluorine and $Y_n$ is 2,4-$(CH_3)_2$ and the radical $X_m$ corresponds to one line of Table A for each compound.

TABLE 33

Compounds of the formula I.1 in which $R^1$ and $R^2$ are methyl and $Y_n$ is 4-chloro and the radical $X_m$ corresponds to one line of Table A for each compound.

TABLE 34

Compounds of the formula I.1 in which $R^1$ and $R^2$ are methyl and $Y_n$ is 3,4-dichloro and the radical $X_m$ corresponds to one line of Table A for each compound.

TABLE 35

Compounds of the formula I.1 in which $R^1$ and $R^2$ are methyl and $Y_n$ is 2,4-dichloro and the radical $X_m$ corresponds to one line of Table A for each compound.

TABLE 36

Compounds of the formula I.1 in which $R^1$ and $R^2$ are methyl and $Y_n$ is 4-fluoro and the radical $X_m$ corresponds to one line of Table A for each compound.

TABLE 37

Compounds of the formula I.1 in which $R^1$ and $R^2$ are methyl and $Y_n$ is 3,4-difluoro and the radical $X_m$ corresponds to one line of Table A for each compound.

TABLE 38

Compounds of the formula I.1 in which $R^1$ and $R^2$ are methyl and $Y_n$ is 2,4-difluoro and the radical $X_m$ corresponds to one line of Table A for each compound.

TABLE 39

Compounds of the formula I.1 in which $R^1$ and $R^2$ are methyl and $Y_n$ is 4-$CH_3$ and the radical $X_m$ corresponds to one line of Table A for each compound.

TABLE 40

Compounds of the formula I.1 in which $R^1$ and $R^2$ are methyl and $Y_n$ is 3,4-$(CH_3)_2$ and the radical $X_m$ corresponds to one line of Table A for each compound.

TABLE 41

Compounds of the formula I.1 in which $R^1$ and $R^2$ are methyl and $Y_n$ is 2,4-$(CH_3)_2$ and the radical $X_m$ corresponds to one line of Table A for each compound.

TABLE 42

Compounds of the formula I.1 in which $R^1$ is methyl, $R^2$ is hydrogen and $Y_n$ is 4-chloro and the radical $X_m$ corresponds to one line of Table A for each compound.

TABLE 43

Compounds of the formula I.1 in which $R^1$ is methyl, $R^2$ is hydrogen and $Y_n$ is 3,4-dichloro and the radical $X_m$ corresponds to one line of Table A for each compound.

TABLE 44

Compounds of the formula I.1 in which $R^1$ is methyl, $R^2$ is hydrogen and $Y_n$ is 2,4-dichloro and the radical $X_m$ corresponds to one line of Table A for each compound.

TABLE 45

Compounds of the formula I.1 in which $R^1$ is methyl, $R^2$ is hydrogen and $Y_n$ is 4-fluoro and the radical $X_m$ corresponds to one line of Table A for each compound.

TABLE 46

Compounds of the formula I.1 in which $R^1$ is methyl, $R^2$ is hydrogen and $Y_n$ is 3,4-difluoro and the radical $X_m$ corresponds to one line of Table A for each compound.

TABLE 47

Compounds of the formula I.1 in which $R^1$ is methyl, $R^2$ is hydrogen and $Y_n$ is 2,4-difluoro and the radical $X_m$ corresponds to one line of Table A for each compound.

TABLE 48

Compounds of the formula I.1 in which $R^1$ is methyl, $R^2$ is hydrogen and $Y_n$ is 4-$CH_3$ and the radical $X_m$ corresponds to one line of Table A for each compound.

TABLE 49

Compounds of the formula I.1 in which $R^1$ is methyl, $R^2$ is hydrogen and $Y_n$ is 3,4-$(CH_3)_2$ and the radical $X_m$ corresponds to one line of Table A for each compound.

TABLE 50

Compounds of the formula I.1 in which $R^1$ is methyl, $R^2$ is hydrogen and $Y_n$ is 2,4-$(CH_3)_2$ and the radical $X_m$ corresponds to one line of Table A for each compound.

TABLE 51

Compounds of the formula I.1 in which $R^1$ is ethyl, $R^2$ is hydrogen and $Y_n$ is 4-chloro and the radical $X_m$ corresponds to one line of Table A for each compound.

TABLE 52

Compounds of the formula I.1 in which $R^1$ is ethyl, $R^2$ is hydrogen and $Y_n$ is 3,4-dichloro and the radical $X_m$ corresponds to one line of Table A for each compound.

TABLE 53

Compounds of the formula I.1 in which $R^1$ is ethyl, $R^2$ is hydrogen and $Y_n$ is 2,4-dichloro and the radical $X_m$ corresponds to one line of Table A for each compound.

TABLE 54

Compounds of the formula I.1 in which $R^1$ is ethyl, $R^2$ is hydrogen and $Y_n$ is 4-fluoro and the radical $X_m$ corresponds to one line of Table A for each compound.

TABLE 55

Compounds of the formula I.1 in which $R^1$ is ethyl, $R^2$ is hydrogen and $Y_n$ is 3,4-difluoro and the radical $X_m$ corresponds to one line of Table A for each compound.

TABLE 56

Compounds of the formula I.1 in which $R^1$ is ethyl, $R^2$ is hydrogen and $Y_n$ is 2,4-difluoro and the radical $X_m$ corresponds to one line of Table A for each compound.

TABLE 57

Compounds of the formula I.1 in which $R^1$ is ethyl, $R^2$ is hydrogen and $Y_n$ is 4-$CH_3$ and the radical $X_m$ corresponds to one line of Table A for each compound.

TABLE 58

Compounds of the formula I.1 in which $R^1$ is ethyl, $R^2$ is hydrogen and $Y_n$ is 3,4-$(CH_3)_2$ and the radical $X_m$ corresponds to one line of Table A for each compound.

TABLE 59

Compounds of the formula I.1 in which $R^1$ is ethyl, $R^2$ is hydrogen and $Y_n$ is 2,4-$(CH_3)_2$ and the radical $X_m$ corresponds to one line of Table A for each compound.

TABLE 60

Compounds of the formula I.1 in which $R^1$ is methoxy, $R^2$ is hydrogen and $Y_n$ is 4-chloro and the radical $X_m$ corresponds to one line of Table A for each compound.

TABLE 61

Compounds of the formula I.1 in which $R^1$ is methoxy, $R^2$ is hydrogen and $Y_n$ is 3,4-dichloro and the radical $X_m$ corresponds to one line of Table A for each compound.

TABLE 62

Compounds of the formula I.1 in which $R^1$ is methoxy, $R^2$ is hydrogen and $Y_n$ is 2,4-dichloro and the radical $X_m$ corresponds to one line of Table A for each compound.

TABLE 63

Compounds of the formula I.1 in which $R^1$ is methoxy, $R^2$ is hydrogen and $Y_n$ is 4-fluoro and the radical $X_m$ corresponds to one line of Table A for each compound.

TABLE 64

Compounds of the formula I.1 in which $R^1$ is methoxy, $R^2$ is hydrogen and $Y_n$ is 3,4-difluoro and the radical $X_m$ corresponds to one line of Table A for each compound.

TABLE 65

Compounds of the formula I.1 in which $R^1$ is methoxy, $R^2$ is hydrogen and $Y_n$ is 2,4-difluoro and the radical $X_m$ corresponds to one line of Table A for each compound.

TABLE 66

Compounds of the formula I.1 in which $R^1$ is methoxy, $R^2$ is hydrogen and $Y_n$ is 4-$CH_3$ and the radical $X_m$ corresponds to one line of Table A for each compound.

TABLE 67

Compounds of the formula I.1 in which $R^1$ is methoxy, $R^2$ is hydrogen and $Y_n$ is 3,4-$(CH_3)_2$ and the radical $X_m$ corresponds to one line of Table A for each compound.

TABLE 68

Compounds of the formula I.1 in which $R^1$ is methoxy, $R^2$ is hydrogen and $Y_n$ is 2,4-$(CH_3)_2$ and the radical $X_m$ corresponds to one line of Table A for each compound.

TABLE 69

Compounds of the formula I.1 in which $R^1$ is trifluoromethoxy, $R^2$ is hydrogen and $Y_n$ is 4-chloro and the radical $X_m$ corresponds to one line of Table A for each compound.

TABLE 70

Compounds of the formula I.1 in which $R^1$ is trifluoromethoxy, $R^2$ is hydrogen and $Y_n$ is 3,4-dichloro and the radical $X_m$ corresponds to one line of Table A for each compound.

TABLE 71

Compounds of the formula I.1 in which $R^1$ is trifluoromethoxy, $R^2$ is hydrogen and $Y_n$ is 2,4-dichloro and the radical $X_m$ corresponds to one line of Table A for each compound.

TABLE 72

Compounds of the formula I.1 in which $R^1$ is trifluoromethoxy, $R^2$ is hydrogen and $Y_n$ is 4-fluoro and the radical $X_m$ corresponds to one line of Table A for each compound.

TABLE 73

Compounds of the formula I.1 in which $R^1$ is trifluoromethoxy, $R^2$ is hydrogen and $Y_n$ is 3,4-difluoro and the radical $X_m$ corresponds to one line of Table A for each compound.

TABLE 74

Compounds of the formula I.1 in which $R^1$ is trifluoromethoxy, $R^2$ is hydrogen and $Y_n$ is 2,4-difluoro and the radical $X_m$ corresponds to one line of Table A for each compound.

TABLE 75

Compounds of the formula I.1 in which $R^1$ is trifluoromethoxy, $R^2$ is hydrogen and $Y_n$ is 4-$CH_3$ and the radical $X_m$ corresponds to one line of Table A for each compound.

TABLE 76

Compounds of the formula I.1 in which $R^1$ is trifluoromethoxy, $R^2$ is hydrogen and $Y_n$ is 3,4-$(CH_3)_2$ and the radical $X_m$ corresponds to one line of Table A for each compound.

TABLE 77

Compounds of the formula I.1 in which $R^1$ is trifluoromethoxy, $R^2$ is hydrogen and $Y_n$ is 2,4-$(CH_3)_2$ and the radical $X_m$ corresponds to one line of Table A for each compound.

TABLE 78

Compounds of the formula I.2 in which $R^1$ and $R^2$ are chlorine and $Y_n$ is 4-chloro, $R^3$ and $R^4$ form a cyclopropyl ring and the radical $X_m$ corresponds to one line of Table A for each compound.

TABLE 79

Compounds of the formula I.2 in which $R^1$ and $R^2$ are fluorine and $Y_n$ is 4-chloro, $R^3$ and $R^4$ form a cyclopropyl ring and the radical $X_m$ corresponds to one line of Table A for each compound.

TABLE 80

Compounds of the formula I.2 in which $R^1$ and $R^2$ are methyl and $Y_n$ is 4-chloro, $R^3$ and $R^4$ form a cyclopropyl ring and the radical $X_m$ corresponds to one line of Table A for each compound.

TABLE 81

Compounds of the formula I.2 in which $R^1$ is methyl, $R^2$ is hydrogen and $Y_n$ is 4-chloro, $R^3$ and $R^4$ form a cyclopropyl ring and the radical $X_m$ corresponds to one line of Table A for each compound.

TABLE 82

Compounds of the formula I.2 in which $R^1$ is ethyl, $R^2$ is hydrogen and $Y_n$ is 4-chloro, $R^3$ and $R^4$ form a cyclopropyl ring and the radical $X_m$ corresponds to one line of Table A for each compound.

TABLE 83

Compounds of the formula I.2 in which $R^1$ is methyl, $R^2$ is hydrogen and $Y_n$ is 4-chloro, $R^3$ and $R^4$ form a cyclopropyl ring and the radical $X_m$ corresponds to one line of Table A for each compound.

TABLE 84

Compounds of the formula I.2 in which $R^1$ is trifluoromethoxy, $R^2$ is hydrogen and $Y_n$ is 4-chloro, $R^3$ and $R^4$ form a cyclopropyl ring and the radical $X_m$ corresponds to one line of Table A for each compound.

TABLE A

| No. | $X_m$ |
| --- | --- |
| A-1 | 2-Cl |
| A-2 | 3-Cl |
| A-3 | 4-Cl |
| A-4 | 2-F |
| A-5 | 3-F |
| A-6 | 4-F |
| A-7 | 2-$CH_3$ |
| A-8 | 3-$CH_3$ |
| A-9 | 4-$CH_3$ |
| A-10 | 2-$CH_2CH_3$ |
| A-11 | 3-$CH_2CH_3$ |
| A-12 | 4-$CH_2CH_3$ |
| A-13 | 3-$CH_2CH_2CH_3$ |
| A-14 | 4-$CH_2CH_2CH_3$ |
| A-15 | 3-$CH(CH_3)_2$ |
| A-16 | 4-$CH(CH_3)_2$ |
| A-17 | 2-$OCH_3$ |
| A-18 | 3-$OCH_3$ |
| A-19 | 4-$OCH_3$ |
| A-20 | 2-$OCH_2CH_3$ |
| A-21 | 3-$OCH_2CH_3$ |
| A-22 | 4-$OCH_2CH_3$ |
| A-23 | 3-$OCH_2CH_2CH_3$ |
| A-24 | 4-$OCH_2CH_2CH_3$ |
| A-25 | 3-$OCH(CH_3)_2$ |
| A-26 | 4-$OCH(CH_3)_2$ |
| A-27 | 2,3-$(CH_3)_2$ |
| A-28 | 3,4-$(CH_3)_2$ |
| A-29 | 3,5-$(CH_3)_2$ |
| A-30 | 2,6-$(CH_3)_2$ |
| A-31 | 2,3-$(CH_2CH_3)_2$ |
| A-32 | 3,4-$(CH_2CH_3)_2$ |
| A-33 | 3,5-$(CH_2CH_3)_2$ |
| A-34 | 2,6-$(CH_2CH_3)_2$ |
| A-35 | 3-$CH_3$, 4-$CH_2CH_3$ |
| A-36 | 3-$CH_2CH_3$, 4-$CH_3$ |
| A-37 | 3-$CH_3$, 5-$CH_2CH_3$ |
| A-38 | 2-$CH_2CH_3$, 6-$CH_3$ |
| A-39 | 2,3-$(OCH_3)_2$ |
| A-40 | 3,4-$(OCH_3)_2$ |
| A-41 | 3,5-$(OCH_3)_2$ |
| A-42 | 2,6-$(OCH_3)_2$ |
| A-43 | 2,3-$(OCH_2CH_3)_2$ |
| A-44 | 3,4-$(OCH_2CH_3)_2$ |
| A-45 | 3,5-$(OCH_2CH_3)_2$ |
| A-46 | 2,6-$(OCH_2CH_3)_2$ |
| A-47 | 3-$OCH_3$, 4-$OCH_2CH_3$ |
| A-48 | 3-$OCH_2CH_3$, 4-$OCH_3$ |
| A-49 | 3-$OCH_3$, 5-$OCH_2CH_3$ |
| A-50 | 2-$OCH_2CH_3$, 6-$OCH_3$ |
| A-51 | 3-$OCH_3$, 4-$OCH_2CH_2CH_3$ |
| A-52 | 3-$OCH_2CH_2CH_3$, 4-$OCH_3$ |
| A-53 | 3-$OCH_2CH_3$, 4-$OCH_2CH_2CH_3$ |
| A-54 | 3-$OCH_2CH_2CH_3$, 4-$OCH_2CH_3$ |
| A-55 | 3-$OCH_3$, 4-$OCH(CH_3)_2$ |
| A-56 | 3-$OCH(CH_3)_2$, 4-$OCH_3$ |
| A-57 | 3-$OCH_3$, 4-$OCH_2$—$C_6H_5$ |
| A-58 | 3-$OCH_2$—$C_6H_5$, 4-$OCH_3$ |
| A-59 | 3,4-$(OCH_2$—$C_6H_5)_2$ |
| A-60 | 3-$OCH_3$, 4-$OCH_2$—CH=$CH_2$ |
| A-61 | 3-$OCH_3$, 4-$OCH_2$—C≡CH |
| A-62 | 3-$OCH_3$, 4-$OCH(CH_3)$—C≡CH |
| A-63 | 3-$OCH_3$, 4-$OCH(CH_3)$—C≡C—$CH_3$ |
| A-64 | 3-$OCH_3$, 4-$OCH(CH_3)$—C≡C—$CH_2CH_3$ |
| A-65 | 3-$OCH_3$, 4-$OC(CH_3)_2$—C≡CH |
| A-66 | 3-$OCH_3$, 4-$OC(CH_3)_2$—C≡C—$CH_3$ |
| A-67 | 3-$OCH_3$, 4-$OC(CH_3)_2$—C≡C—$CH_2CH_3$ |
| A-68 | 3-$OCH_3$, 4-$OCH_2$—C≡C—$C_6H_5$ |
| A-69 | 3-$OCH_3$, 4-$OCH(CH_3)$—C≡C—$C_6H_5$ |
| A-70 | 3-$OCH_3$, 4-$OC(CH_3)_2$—C≡C—$C_6H_5$ |
| A-71 | 3-$OCH_3$, 4-$OCH_2$—C≡C-(4-Cl—$C_6H_4$) |
| A-72 | 3-$OCH_3$, 4-$OCH(CH_3)$—C≡C-(4-Cl—$C_6H_4$) |
| A-73 | 3-$OCH_3$, 4-$OC(CH_3)_2$—C≡C-(4-Cl—$C_6H_4$) |
| A-74 | 3-$OCH_3$, 4-$OCF_3$ |
| A-75 | 3-$OCH_3$, 4-$OCHF_2$ |

The compounds I are suitable as fungicides. They are distinguished by an outstanding activity against a broad spectrum of phytopathogenic fungi, in particular from the classes of the Ascomycetes, Deuteromycetes, Phycomycetes and Basidiomycetes. Some of the act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

Alternaria species on vegetables and fruit,
*Botrytis cinerea* (gray mold) on strawberries, vegetables, ornamentals and grapevines,
*Cercospora arachidicola* on peanuts,
*Erysiphe cichoracearum* and *Sphaerotheca fuliginea* on cucurbits
*Erysiphe graminis* (powdery mildew) on cereals,
Fusarium and Verticillium species on various plants, Helminthosporium species on cereals,
Mycosphaerella species on bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
Pseudoperonospora species on hops and cucumbers,
Puccinia species on cereals,
*Pyricularia oryzae* on rice,
Rhizoctonia species on cotton, rice and lawns,
*Septoria nodorum* on wheat,
*Uncinula necator* on grapevines,
Ustilago species on cereals and sugar cane, and
Venturia species (scab) on apples and pears.

Moreover, the compounds I are suitable for controlling fungal pests such as *Paecilomyces variotii* in the protection of materials (e.g. wood, paper, paint dispersions, fibers and tissues) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise between 0.1 and 95, preferably between 0.5 and 90%, by weight of active ingredient.

When used in crop protection, the application rates are between 0.01 and 2.0 kg of active ingredient per ha, depending on the nature of the desired effect.

In the treatment of seed, amounts of active ingredient of from 0.001 to 0.1 g, preferably 0.01 to 0.05 g, are generally required per kilogram of seed.

When used in the protection of materials or stored products, the application rate of active ingredient depends on the nature of the field of application and on the desired effect. Application rates which are conventionally used in the protection of materials are, for example, 0.001 g to 2 kg, preferably 0.005 g to 1 kg, of active ingredient per cubic meter of material treated.

The compounds I can be converted into the customary formulations, e.g. solutions, emulsions, suspensions, dusts, powders, pastes and granules. The use form depends on the particular purpose; in any case, it should guarantee a fine and uniform distribution of the compound according to the invention.

The formulations are prepared in a known manner, e.g. by extending the active ingredient with solvents and/or carriers, if desired using emulsifiers and dispersants, it also being possible to use other organic solvents as cosolvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethyl formamide) and water; carriers such as ground natural minerals (e.g. kaolins, clays, talc, chalk) and ground synthetic minerals (e.g. highly-disperse silica, silicates); emulsifiers such as nonionic and anionic emulsifiers (e.g. polyoxyethylene fatty alcohol ethers, alkylsulfonates and arylsulfonates) and dispersants such as lignin-sulfite waste liquors and methyl cellulose.

Suitable surfactants are alkali metal, alkaline earth metal and ammonium salts of ligninsulfonic acid, naphthalene sulfonic acid, phenol sulfonic acid, dibutylnaphthalene sulfonic acid, alkylaryl sulfonates, alkyl sulfates, alkyl sulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of naphthalene sulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable and animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone, and water.

Powders, materials for spreading and dusts can be prepared by mixing or grinding the active substances together with a solid carrier.

Granules, e.g. coated granules, impregnated granules and homogeneous granules, can be prepared by binding the active ingredients to solid carriers. Examples of solid carriers are mineral earths, such as silica gel, silicas, silica gels [sic], silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from between 0.01 and 95% by weight, preferably between 0.1 and 90% by weight, of the active ingredient. The active ingredients are employed in a purity of from 90% to 100%, preferably from 95% to 100% (according to NMR spectrum).

Examples of Formulations are

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which has been sprayed onto the surface of this silica gel. This gives a formulation of the active ingredient with good adhesion properties (active ingredient content 23% by weight).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (active ingredient content 9% by weight).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (active ingredient content 16% by weight).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (active ingredient content 80% by weight).

VI. 90 parts by weight of a compound according to the invention are mixed with 10 parts by weight of N-methyl-α-pyrrolidone, which gives a solution which is suitable for use in the form of microdrops (active ingredient content 90% by weight).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-a-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; in any case, it is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use preparations can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides, fungicides, other pesticides, or bactericides may be added to the active ingredients, if appropriate also only immediately prior to use (tank mix). These can be admixed with the compositions according to the invention in a weight ratio of 1:10 to 10:1.

In the use form as fungicides, the compositions according to the invention can also be present together with other active ingredients, the [sic] eg. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides [sic], ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)benzimidazole, N-(1,1, 2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide,N-cyclohexyl-N-methoxy-2,5-di-methylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichlorethane; 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolyl-urea, 1-(4- chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)-oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurins such as methyl E-methoxyimino-[α-(o-tolyloxy)-o-tolyl]acetate, methyl E-2-{2-[6-(2-cyanophenoxy)pyrimidin-4-yloxy]-phenyl}-3-methoxyacrylate, methyl-E-methoxyimino-[α-(2-phenoxyphenyl)]acetamide, methyl-E-methoxyimino-[α-(2,5-dimethylphenoxy)-o-tolyl]acetamide, anilinopyrimidines such as N-(4,6-dimethylpyrimidin-2-yl)aniline, N-[4-methyl-6-(1-propynyl)pyrimidin-2-yl]aniline, N-[4-methyl-6-cyclopropylpyrimidin-2-yl]aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxy-phenyl)acryloylmorpholine, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-amino-butyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichloro-phenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

SYNTHESIS EXAMPLES

With due modification of the starting compounds, the protocols shown in the synthesis examples below were used for obtaining further compounds I. The resulting compounds, together with physical data, are listed in the table which follows.

Example 1

Preparation of Methyl 2-bromo-(4-Chlorophenyl) acetate 116 g (0.585 mol) of 1,3-dibromo-5,5-dimethylhyntantoin [sic] and 1 g of AIBN were added portionwise to the solution of 215.3 g (1.17 mol) of methyl 4-chlorophenylacetate in 500 ml of tetrachloromethane, and the mixture was refluxed for 24 hours. This was followed by washing with water and 1 N sodium hydroxide solution, the aqueous phases were extracted with methylene chloride, and the organic phases were dried and concentrated. This gave 260 g of the title compound.

$^1$H NMR [δ, (CDCl$_3$)]: 3.8 (s, 3H); 5.3 (s, 1H).

Example 2

Preparation of Methyl (4-Chlorophenyl)-2-oxoacetate 97.2 g of a 75% strength aqueous N-methylmorpholine N-oxide solution were added with ice-cooling to a solution of 100 g (0.38 mol) of the compound of Example 1 in 400 ml of dimethyl sulfoxide (DMSO). After the mixture had been stirred for 24 hours at 20 to 25° C., it was poured into water and extracted with methyl tert-butyl ether (MtBE). After the organic phases had been dried, stripped from the solvent and chromatographed on silica gel (cyclohexane/MtBE [3:1]), 69 g of the title compound was obtained.

$^1$H NMR [δ, (CDCl$_3$)]: 4.0 (s, 3H); 7.5 (m, 2H) and 8.0 (m, 2H).

Example 3

Preparation of Methyl 3,3-dichloro-2-(4-Chlorophenyl)acrylate

A solution of 29.9 g (0.15 mol) of the keto ester of Example 2 in 300 ml of acetonitrile were treated with 117.9 g of PPh$_3$ (0.45 mol), and 69.3 g (0.45 mol) of carbon tetrachloride were then added dropwise. After the reaction solution had remained at approximately 56° C. for 4 hours, it was concentrated; the residue obtained was chromatographed over silica gel with cyclohexane/MtBE (3:1). This gave 39.2 g of the title compound.

$^1$H NMR [δ, (CDCl$_3$)]: 3.8 (s, 3H); 7.3–7.4 (m, 4H).

Example 4

Preparation of 3,3-dichloro-2-(4-Chlorophenyl) acrylic Acid

A solution of 17.1 g (64 mmol) of the ester of Example 3 in 50 ml of methanol was treated with 193 ml of 1 N KOH solution and then stirred for 20 hours at 20 to 25° C. After the solvent had been distilled off, the residue was acidified with 20% strength H$_2$SO$_4$ to pH 1 and extracted with ethyl acetate. The organic phases were dried and stripped from the solvent, whereupon 15 g of the title compound were isolated.

$^1$H NMR [δ, (CDCl$_3$)]: 7.25 (m, 2H); 7.40 (m, 2H) and 9.5 (s, 1H).

Example 5

Preparation of 3,3-dichloro-2-(4-Chlorophenyl) acryloyl Chloride 35.5 g (0.298 mol) of thionyl chloride were added dropwise at 0° C. to the solution of 50 g (0.199 mol) of the acid of Example 4 in 200 ml of diethyl ether and 23.6 g (0.298 mol) of pyridine. The solution was stirred for 6 hours at 20 to 25° C. and then filtered. After the solvent had been distilled off, 42.1 g of the product were obtained, and this was reacted further without purification.

Example 6

Preparation of 3,3-dichloro-2-(4-Chlorophenyl)-N-[2-(3,4-dimethoxy-phenyl)ethyl]acrylamide [I-1]

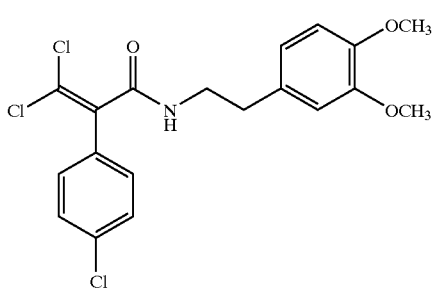

A solution of 10.8 g (0.04 mol) of the acyl chloride prepared in Example 5 in 20 ml of methylene chloride was added dropwise to a solution of 7.24 g (0.04 mol) of homoveratrylamine and 4.04 g 25 (0.04 mol) of triethylamine in 80 ml of methylene chloride. The solution was stirred for 3 hours at 20 to 25° C., and washed with 3 N sodium hydroxide solution and then with 10% by weight strength hydrochloric acid. The organic phase was freed from solvent, and 13.85 g of the title compound were obtained from the residue following chromatography on silica gel with cyclohehane [sic]/MtBE (3:1).

$^1$H NMR [δ, (CDCl$_3$)]: 2.8 (m, 2H); 3.55 (m, 2H); 3.8 (s, 3H); 3.85 (s, 3H); 5.6 (s, 1H); 6.60–6.80 (m, 3H); 7.25–7.40 (m, 4H).

Example 7

Preparation of 4-(2-Aminoethyl)-2-methoxyphenol

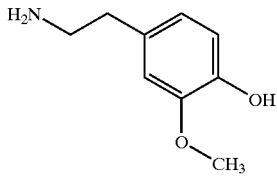

0.5 g of palladium on charcoal (10%) were added to 5 g (19.5 mmol) of 2-[4-(benzyloxy)-3-methoxyphenyl]ethylamine [cf.: Heterocycles, Vol. 28, 297–298 (1989)] in 100 ml of tetrahydrofuran and the mixture was hydrogenated under atmospheric pressure. After the uptake of hydrogen had ended, the mixture was filtered and the filtrate was freed from the solvent.

The residue was triturated with diisopropyl ether, filtered and dried.

IR (cm$^{-1}$): 2935, 1593, 1515, 1263, 1230, 1032.

Example 8

Preparation of 3,3-dichloro-2-(4-Chlorophenyl)-N-[2-(4-hydroxy-3-methoxyphenyl)ethyl]acrylamido-4-(2-aminoethyl)-2-methoxyphenol [I-52]

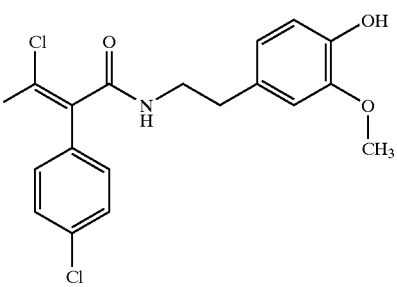

1 g of 4-(2-aminoethyl)-2-methoxyphenol, 2.21 g of 1-benzotriazolyloxy-tris(dimethylamino)phosphonium hexafluorophosphate (BOP) and 1.5 g of N-ethyldiisopropylamine were added to 1.25 g of 3,3-dichloro-2-(4-chlorophenyl)acryloyl chloride in 30 ml of dimethylformamide (DMF), and stirring was continued for approximately 12 hours at 23° C. The mixture was then treated with water and extracted with ethyl acetate, and the extracts were washed with NaCl solution and dried. After the solvent had been removed, the residue was chromatographed over silica gel using cyclohexane/methyl tert-butyl ether (MtBE) (3:1). This gave the title compound in the form of an oil.

MS (m/e): M+H 400, 368, 366, 360.

Example 9

Preparation of 3,3-dichloro-2-(4-Chlorophenyl)-N-[2-(4-hydroxy-3-methoxyphenyl)ethyl]acrylamide [I-53]

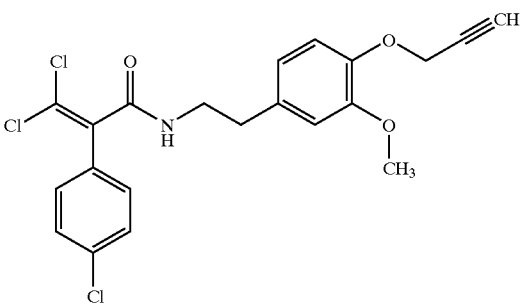

0.14 g of potassium carbonate and 0.12 g of propargyl bromide were added to a solution of 0.4 g of 3,3-dichloro-2-(4-chlorophenyl)-N-[2-(4-hydroxy-3-methoxyphenyl)-ethyl]acrylamide in 50 ml of DMF, the mixture was stirred for approximately 12 hours at 23° C. After a further 0.14 g of potassium carbonate and 0.12 g of propargyl bromide had been added and the mixture had been stirred for a further 6 hours at 23° C., the mixture was poured into water and extracted with MtBE, and the extracts were washed with water and dried. After removal of the solvent and chromatography on silica gel [cyclohexane/MtBE (1:1)], the title compound was obtained in the form of an oil.

$^1$H-NMR (ppm): 2.5 (m, 1H); 2.8 (t, 2H); 3.6 (m, 2H); 3.8 (s, 3H); 4.78 (s, 2H).

TABLE I

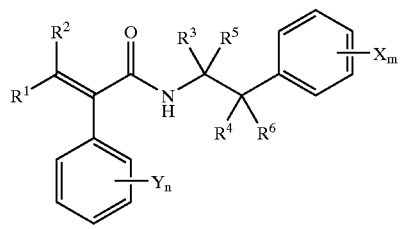

I

| No. | R$^1$ | R$^2$ | R$^3$ | R$^4$ | R$^5$ | R$^6$ | Y$_n$ | X$_m$ | Physical data (Mp. [° C.]; $^1$H NMR δ [ppm]) |
|---|---|---|---|---|---|---|---|---|---|
| I-1 | Cl | Cl | H | H | H | H | 4-Cl | 3,4-(OCH$_3$)$_2$ | 125–130 |
| I-2 | Cl | Cl | H | H | H | H | 4-Cl | 3-OCH$_3$, 4-OCH$_2$CH$_3$ | 103–108 |
| I-3 | Cl | Cl | H | H | H | H | 4-Cl | 2,3,4-(OCH$_2$CH$_3$)$_3$ | 87–88 |
| I-4 | Cl | Cl | H | H | H | H | 4-Cl | 3,4-(OCH$_2$CH$_3$)$_2$ | 111–121 |
| I-5 | Cl | Cl | H | H | H | H | 2-Cl | 3-OCH$_3$,4-OCH$_2$CH$_3$ | 1.4(t); 2.8(m); 3.6(m); 3.8(s) |
| I-6 | Cl | Cl | H | H | H | H | 2-Cl | 3,4-(OCH$_2$CH$_3$)$_2$ | 1.4(t); 2.7(m); 3.6(m); 4.0(s) |
| I-7 | Cl | Cl | H | H | H | H | 2-F | 3,4-(OCH$_3$)$_2$ | 82–85 |
| I-8 | Cl | Cl | H | H | H | H | 2-F | 3-OCH$_3$, 4-OCH$_2$CH$_3$ | 97–100 |
| I-9 | Cl | Cl | H | H | H | H | 2-F | 3,4-(OCH$_2$CH$_3$)$_2$ | 92–95 |
| I-10 | Cl | Cl | H | H | H | H | 3,4-Cl$_2$ | 3,4-(OCH$_3$)$_2$ | 124–127 |
| I-11 | Cl | Cl | H | H | H | H | 3,4-Cl$_2$ | 3-OCH$_3$, 4-OCH$_2$CH$_3$ | 110–113 |
| I-12 | Cl | Cl | H | H | H | H | 3,4-Cl$_2$ | 3,4-(OCH$_2$CH$_3$)$_2$ | 115 |
| I-13 | Cl | Cl | H | H | H | H | 2,4-Cl$_2$ | 3,4-(OCH$_3$)$_2$ | 2.8(m); 3.6(m); 3.92(s); 3.95(s) |
| I-14 | Cl | Cl | H | H | H | H | 2,4-Cl$_2$ | 3-OCH$_3$, 4-OCH$_2$CH$_3$ | 1.4(t); 2.7(m); 3.5(m); 3.8(s) |
| I-15 | Cl | Cl | H | CH(CH$_3$)$_2$ | H | CH(CH$_3$)$_2$ | 4-Cl | 3,4-(OCH$_3$)$_2$ | 157–160 |
| I-16 | CH$_2$CH$_3$ | H | H | H | H | H | 4-Cl | 3,4-(OCH$_3$)$_2$ | 1.0(t); 1.9(m); 2.8(t); 3.4(m) |
| I-17 | CH$_2$CH$_3$ | H | H | H | H | H | 4-Cl | 3-OCH$_3$, 4-OCH$_2$CH$_3$ | 1.0(t); 1.5(t); 2.0(m); 2.7(t) |
| I-18 | CH$_3$ | H | H | H | H | H | 4-Cl | 3,4-(OCH$_3$)$_2$ | 1.6(d); 2.7(t); 3.5(m); 3.8(s) |
| I-19 | CH$_3$ | H | H | H | H | H | 4-Cl | 3-OCH$_3$, 4-OCH$_2$CH$_3$ | 1.5(t); 1.6(d); 2.7(m); 3.5(m) |
| I-20 | CH$_3$ | H | H | H | H | H | 4-F | 3-OCH$_3$, 4-OCH$_2$CH$_3$ | 1.5(t); 2.7(m); 3.3(m); 3.8(s) |
| I-21 | CH$_3$ | H | H | H | H | H | 4-CF$_3$ | 3-OCH$_3$, 4-OCH$_2$CH$_3$ | 1.5(d); 1.6(t); 2.7(t); 3.5(m) |
| I-22 | CH$_3$ | H | H | H | H | H | 4-C(CH$_3$)$_3$ | 3-OCH$_3$, 4-OCH$_2$CH$_3$ | 1.3(s); 1.5(t); 1.7(d); 2.7(t) |
| I-23 | CH$_2$CH$_3$ | H | H | H | H | H | H | 3-OCH$_3$, 4-OCH$_2$CH$_3$ | 1.0(t); 1.5(t); 2.0(m); 2.7(t) |
| I-24 | CH$_2$CH$_3$ | H | H | H | H | H | 4-F | 3-OCH$_3$, 4-OCH$_2$CH$_3$ | 1.0(t); 1.5(t); 1.9(m); 2.7(m) |
| I-25 | CH$_2$CH$_3$ | H | H | H | H | H | 4-CH$_3$ | 3-OCH$_3$, 4-OCH$_2$CH$_3$ | 1.0(t); 1.5(t); 2.0(m); 2.3(s) |
| I-26 | CH$_2$CH$_3$ | H | H | H | H | H | 4-CF$_3$ | 3-OCH$_3$, OCH$_2$CH$_3$ | 1.0(t); 1.5(t); 1.9(m); 2.7(m); 3.5(m) |
| I-27 | CH$_2$CH$_3$ | H | H | H | H | H | 3,4-Cl$_2$ | 3-OCH$_3$, 4-OCH$_2$CH$_3$ | 1.0(m); 1.5(m); 2.3(m); 2.8(t); 3.6(m) |
| I-28 | CH$_2$CH$_3$ | H | H | H | H | H | 2,4-Cl$_2$ | 3-OCH$_3$, 4-OCH$_2$CH$_3$ | 1.1(t); 1.5(t); 2.6(m); 2.7(m); 3.5(m) |
| I-29 | CH$_2$CH$_3$ | H | H | H | H | H | 3-CH$_3$ | 3-OCH$_3$, 4-OCH$_2$CH$_3$ | 1.0(t); 1.4(t); 2.7(t); 3.5(s); 3.8(s) |
| I-30 | CH$_2$CH$_3$ | H | H | H | H | H | 2-F, 4-CH$_3$ | 3-OCH$_3$, 4-OCH$_2$CH$_3$ | 1.0(t); 1.5(t); 1.9(m); 2.4(s); 2.7(t) |
| I-31 | CH$_2$CH$_3$ | H | H | H | H | H | 3,5-Cl$_2$ | 3-OCH$_3$, 4-OCH$_2$CH$_3$ | 1.0(t); 1.4(m); 2.0(m); 2.7(t) |
| I-32 | H | CH$_2$CH$_3$ | H | H | H | H | 4-Cl | 3-OCH$_3$, 4-OCH$_2$CH$_3$ | 1.0(t); 1.4(t); 2.2(m); 3.7(m) |
| I-33 | Cl | Cl | H | H | H | H | 4-OCH$_3$ | 3,4-(OCH$_3$)$_2$ | 111–113 |
| I-34 | Cl | Cl | H | H | H | H | 4-OCH$_3$ | 3-OCH$_3$, 4-OCH$_2$CH$_3$ | 91–93 |
| I-35 | Cl | Cl | H | H | H | H | 4-OCH$_3$ | 3,4-(OCH$_2$CH$_3$)$_2$ | 128–129 |
| I-36 | Cl | Cl | H | H | H | H | 4-OCH$_3$ | 3-OCH$_2$CH$_3$, 4-OCH$_3$ | 113–115 |
| I-37 | Cl | Cl | H | H | H | H | 3-CF$_3$ | 3-OCH$_3$, 4-OCH$_2$CH$_3$ | 2.8(t); 3.5(m); 3.8(s); 3.9(s) |
| I-38 | Cl | Cl | H | H | H | H | 4-Cl | 3-OCH$_2$CH$_3$, 4-OCH$_3$ | 1.5(t); 2.8(t); 3.6(m); 3.9(s); 4.0(m) |

TABLE I-continued

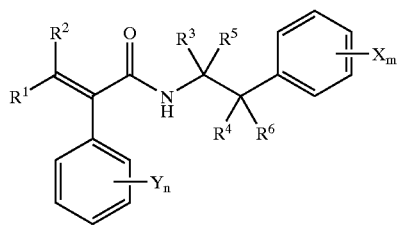

I

| No. | $R^1$ | $R^2$ | $R^3$ | $R^4$ | $R^5$ | $R^6$ | $Y_n$ | $X_m$ | Physical data (Mp. [° C.]; $^1$H NMR δ [ppm]) |
|---|---|---|---|---|---|---|---|---|---|
| I-39 | Cl | Cl | H | H | H | H | 4-C(CH$_3$)$_3$ | 3-OCH$_3$, 4-OCH$_2$CH$_3$ | 1.3(s); 1.5(t); 2.8(t); 3.5(m) |
| I-40 | Cl | Cl | H | H | H | H | 4-C(CH$_3$)$_3$ | 3,4-(OCH$_3$)$_2$ | 1.3(s); 2.8(t); 3.6(m); 3.8(s) |
| I-41 | Cl | Cl | H | H | H | H | 4-C(CH$_3$)$_3$ | 3,4-(OCH$_2$CH$_3$)$_2$ | 1.3(s); 1.6(t); 2.8(t); 3.6(m) |
| I-42 | Cl | Cl | H | H | H | H | 4-C$_6$H$_5$ | 3-OCH$_3$, 4-OCH$_2$CH$_3$ | 138–139 |
| I-43 | Cl | Cl | H | H | H | H | 4-C$_6$H$_5$ | 3,4-(OCH$_3$)$_2$ | 133–135 |
| I-44 | Cl | Cl | H | H | H | H | 4-C$_6$H$_5$ | 3,4-(OCH$_2$CH$_3$)$_2$ | 124–125 |
| I-45 | Cl | Cl | H | H | H | H | 4-C$_6$H$_5$ | 3-OCH$_3$, 4-OCH$_2$CH$_3$ | 112–113.5 |
| I-46 | Cl | Cl | H | H | H | H | 4-Br | 3,4-(OCH$_3$)$_2$ | 124–126 |
| I-47 | Cl | Cl | H | H | H | H | 4-Br | 3,4-(OCH$_2$CH$_3$)$_2$ | 126–127 |
| I-48 | CH$_3$ | CH$_3$ | H | H | H | H | 4-Cl | 3,4-(OCH$_3$)$_2$ | 1.6(s); 2.1(s); 2.7(s); 3.6(s); 3.8(s) |
| I-49 | CH$_3$ | CH$_3$ | H | H | H | H | 4-Cl | 3-OCH$_3$, 4-OCH$_2$CH$_3$ | 1.4(t); 2.1(s); 2.7(s); 3.6(s); 3.8(s) |
| I-50 | CH$_3$ | CH$_3$ | H | H | H | H | 4-Cl | 3,4-(OCH$_2$CH$_3$)$_2$ | 1.4(m); 1.7(s); 2.1(s); 2.7(s) |
| I-51 | OCH$_3$ | H | H | H | H | H | 4-Cl | 3-OCH$_3$, 4-OCH$_2$CH$_3$ | 95–98 |
| I-52 | Cl | Cl | H | H | H | H | 4-Cl | 3-OCH$_3$, 4-OH | see Example 8 |
| I-53 | Cl | Cl | H | H | H | H | 4-Cl | 3-OCH$_3$, 4-OCH$_2$C≡CH | see Example 9 |

Examples of the Action Against Fungal Pests

The fungicidal action of the compounds of the formula I was demonstrated by the following experiments:

The active ingredients were formulated separately or jointly as a 10% strength emulsion in a mixture of 70% by weight of cyclohexanone, 20% by weight of Nekanil® LN (Lutensol® AP6, wetter with emulsifying and dispersing action based on ethoxylated alkyl phenols) and 10% by weight of Wettol® EM (nonionic emulsifier based on ethoxylated castor oil) and diluted with water to give the desired concentration.

Use Example 1—Efficacy Against Phytophthora Infestans on Tomatoes

Leaves of potted plants cv. "GroBe Fleischtomate St. Pierre" were sprayed to runoff point with an aqueous suspension made with a stock solution of 10% active ingredient, 63% cyclohexanone and 27% emulsifier. The next day, the leaves were infected with a cold aqueous zoospore suspension of Phytophthora infestans at a density [sic] of 0.25×10$^6$ spores/ml. Then, the plants were replaced into a chamber with 100% atmospheric humidity at temperatures between 18 and 20° C. After 6 days, the blight had developed to such an extent on the untreated, but infected, control plants that it was possible to visually determine the disease level in percent.

In this test, the plants which had been treated with 250 ppm of the active ingredients I-1, I-2, I-11, I-17, I-19, I-25, I-26, I-27, I-32, I-33, I-34, I-39, I-40, I-42, I-43, I-45, I-46 and I-49 of table I showed a disease level of not more than 10%, while the disease level of the untreated plants was 90%.

Use Example 2—Efficacy Against Plasmopara viticola

Leaves of potted grapevines of the variety "Müller-Thurgau" were sprayed to runoff point with an aqueous active ingredient preparation made with a stock solution of 10% active ingredient, 63% cyclohexanone and 27% emulsifier. The next day, the leaves were inoculated with an aqueous zoospore suspension of Plasmopara viticola. Then, the grapevines were first placed for 48 hours into a chamber at 24° C. and 100% atmospheric humidity and then for 5 days in a greenhouse at temperatures between 20 and 30° C. After this time, the plants were returned for 16 hours into a humid chamber to accelerate the eruption of sporangiophores. The extent to which the disease had developed on the undersides of the leaves was then determined visually.

In this test, the plants which had been treated with 250 ppm of the active ingredients I-1, I-2, I-10, I-11, I-12, I-16, I-17, I-19, I-21 to I-27, I-29, I-30, I-32, I-33, I-34, I-39, I-40, I-42, I-43, I-45, I-46, I-48 and I-49 of table I showed a disease level of not more than 10%, while the disease level of the untreated plants was 90%.

Comparative Experiment—Long-Term Action Against *Phytophthora infestans* on Tomatoes Tomato plants cv. "Große Fleischtomate St. Pierre" in the 4-leaf stage were sprayed to run off point with an aqueous suspension made with a stock solution of 10% active ingredient, 63% cyclohexanone and 27% emulsifier. To test the long-term action of the compounds, the leaves were infected with an aqueous zoospore suspension of *Phytophthora infestans* one week after application. The plants were subsequently placed in a chamber with 100% atmospheric humidity at temperatures between 16 and 18° C. After 6 days, the blight had developed to such an extent on the untreated, but infected, control plants that it was possible to visually determine the disease level in %.

The compound of the structure below, which is known from WO-A 96/23763, acted as comparative active ingredient:

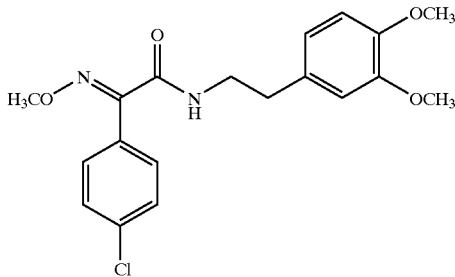

In this test, the plants which had been treated with 63 ppm of the active ingredients I-1, I-2, I-11, I-33 and I-34 of table I showed a disease level of zero to 25%, while the plants which had been treated with 63 ppm of the comparative active ingredient showed a disease level of 40% and the untreated plants showed a disease level of 100%.

We claim:

1. A phenethylacrylamide of the formula I:

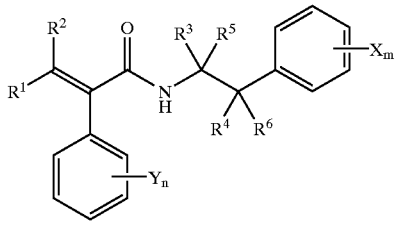

in which the substituents have the following meanings:

X is halogen, $C_1-C_4$-alkyl, $C_1-C_4$-haloalkyl, $C_1-C_8$-alkoxy, $C_1-C_4$-haloalkoxy and —O—C($R^a,R^b$)—C≡C—$R^c$;

$R^a,R^b$ independently of one another are hydrogen and $C_1-C_6$-alkyl;

$R^c$ is hydrogen, $C_1-C_8$-alkyl, $C_3-C_8$-cycloalkyl and phenyl which can be substituted by halogen, cyano, nitro $CF_3$, $C_1-C_4$-alkyl and/or $C_1-C_4$-alkoxy;

m is 1 to 4, it being possible for the radicals X to be different if m is greater than 1;

n is 1 or 2; it being possible for the radicals Y to be different if n is 2;

Y is halogen, nitro, cyano, $C_1-C_4$-alkyl, $CF_3$, $C_1-C_4$-alkoxy and phenyl, Y being in the 3-, 4- or 3,4-position;

$R^1$, $R^2$ independently of one another are hydrogen, halogen, $C_1-C_4$alkyl, $C_1-C_4$-alkoxy, $C_1-C_4$-haloalkoxy and $CF_3$;

$R^3,R^4,R^5,R^6$ independently of one another are hydrogen, $C_1-C_4$-alkyl and $C_1-C_4$-alkoxy or $R^3$ and $R^4$ together form a cyclopropyl ring, it being possible for the C—$R^5$- and C—$R^6$-bonds to be in the E- or Z-position relative to each other;

for controlling phytopathogenic fungal pests.

2. A phenethylacrylamide of the formula I as claimed in claim 1 wherein $R^1$ and $R^2$ are identical and are Cl, F and $CH_3$.

3. A phenethylacrylamide of the formula I as claimed in claim 1 where m is 1 or 2 and X is in the 3-, 4- or 3,4-position.

4. A phenethylacrylamide of the formula I as claimed in claim 1 where X is $C_1-C_8$-alkoxy and Y is halogen.

5. A phenethylacrylamide of the formula I as claimed in claim 1 wherein $R^3$ and $R^4$ are hydrogen.

6. A phenethylacrylamide of the formulae:

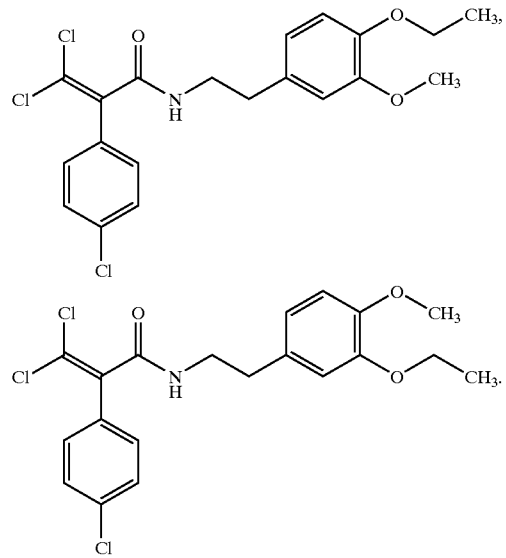

7. A process for the preparation of a compound of claim 2, which comprises α-keto esters of the formula II:

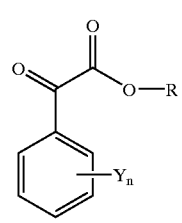

where R is $C_1-C_4$-alkyl with triphenylphosphine and, if $R^1$ and $R^2$ are chlorine, with $CCl_4$, or, if $R^1$ and $R^2$ are fluorine, with sodium difluorochloroacetate, or, if $R^1$ and $R^2$ are methyl, with isopropyltriphenylphosphonium halide under basic conditions to give acrylic esters of the formula III:

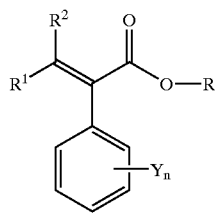
III and hydrolyzing III to give carboxylic acids of the formula IV:

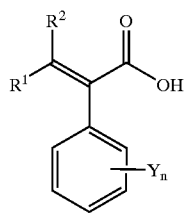
IV and subjecting IV to a condensation reaction with phenethylamines of the formula V:

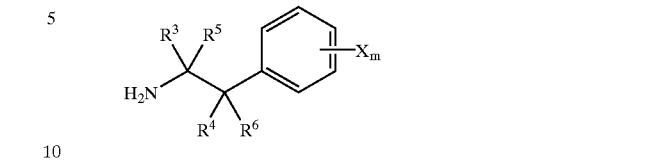
V to give compounds of the formula I.

8. A composition which is suitable for controlling phytopathogenic harmful fungi, comprising a solid or liquid carrier and a compound of the formula I as claimed in claim 2.

9. A method of controlling phytopathogenic harmful fungi, which comprises treating the fungi or the materials, plants, the soil or seed to be protected from fungal infection with an effective amount of a compound of the formula I as claimed in claim 1.

* * * * *